US010316648B2

(12) United States Patent
Swett (10) Patent No.: US 10,316,648 B2
(45) Date of Patent: Jun. 11, 2019

(54) METHOD OF ESTIMATING MULTI-PHASE FLUID PROPERTIES IN A WELLBORE UTILIZING ACOUSTIC RESONANCE

(71) Applicant: Baker Hughes Incorporated, Houston, TX (US)

(72) Inventor: Dwight W. Swett, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 126 days.

(21) Appl. No.: 14/705,523

(22) Filed: May 6, 2015

(65) Prior Publication Data

US 2016/0326866 A1 Nov. 10, 2016

(51) Int. Cl.
*B06B 1/06* (2006.01)
*E21B 47/10* (2012.01)
(Continued)

(52) U.S. Cl.
CPC .......... *E21B 47/101* (2013.01); *B06B 1/0614* (2013.01); *E21B 49/087* (2013.01);
(Continued)

(58) Field of Classification Search
CPC ....... G01H 3/06; E21B 49/082; E21B 47/101; E21B 2049/085; G01N 29/036; G01N 9/002
(Continued)

(56) References Cited

U.S. PATENT DOCUMENTS

| 4,117,716 A | * | 10/1978 | Simon | G01N 9/002 73/32 A |
|---|---|---|---|---|
| 5,348,002 A | | 9/1994 | Caro | |

(Continued)

FOREIGN PATENT DOCUMENTS

WO    WO2014078471 A1    5/2014

OTHER PUBLICATIONS

International Search Report and Written Opinion for International Application No. PCT/US2016/030586; International Filing Date May 3, 2016; dated Sep. 1, 2016 (pp. 1-17).

(Continued)

*Primary Examiner* — Daniel S Larkin
*Assistant Examiner* — David L Singer
(74) *Attorney, Agent, or Firm* — Bracewell LLP; Keith R. Derrington (57) ABSTRACT

A system and method of estimating properties of a wellbore fluid that directs the fluid through a cavity, and generates acoustic waves in the fluid while in the cavity. The acoustic waves are generated by oscillating an electroactive material over a range of frequencies. An electrical admittance spectra of the electroactive material is measured over the range of frequencies; where the electrical admittance spectra includes the magnitude, real, and imaginary components. Differences between the maximum values for each component and a vacuum electrical spectra are calculated, the differences are substituted into estimator equations to estimate the fluid properties. Electrical admittance spectra of the electroactive material was simulated for a series of known fluids flowing through the cavity, and a multi-regression statistical analysis was then used to derive the estimator equations.

17 Claims, 7 Drawing Sheets

(51) Int. Cl.
*E21B 49/08* (2006.01)
*G01N 29/036* (2006.01)
(52) U.S. Cl.
CPC .......... *G01N 29/036* (2013.01); *E21B 49/08* (2013.01); *G01N 2291/014* (2013.01); *G01N 2291/02433* (2013.01); *G01N 2291/02809* (2013.01); *G01N 2291/02818* (2013.01); *G01N 2291/101* (2013.01)
(58) Field of Classification Search
USPC ..... 73/152.28, 152.16, 152.23, 64.53, 61.45, 73/19.1, 61.61, 152.58, 152.55; 702/76, 702/12, 13, 54
See application file for complete search history.

(56) References Cited

U.S. PATENT DOCUMENTS

| | | | |
|---|---|---|---|
| 6,135,234 A | 10/2000 | Harris et al. | |
| 6,250,131 B1* | 6/2001 | Pauley | B01D 19/0042 422/93 |
| 6,709,856 B2* | 3/2004 | Matsumoto | G01N 27/403 435/176 |
| 6,938,470 B2 | 9/2005 | DiFoggio et al. | |
| 6,971,259 B2 | 12/2005 | Gysling | |
| 7,152,460 B2 | 12/2006 | Gysling et al. | |
| 7,380,438 B2 | 6/2008 | Gysling et al. | |
| 7,523,640 B2 | 4/2009 | DiFoggio et al. | |
| 7,661,302 B2 | 2/2010 | Gysling | |
| 7,748,265 B2 | 7/2010 | Reid et al. | |
| 8,032,311 B2 | 10/2011 | DiFoggio | |
| 8,061,186 B2 | 11/2011 | Gysling | |
| 8,085,156 B2 | 12/2011 | Schumacher et al. | |
| 8,175,822 B2 | 5/2012 | Baron et al. | |
| 8,396,676 B2 | 3/2013 | Zozulya et al. | |
| 8,612,154 B2 | 12/2013 | Hsu | |
| 8,640,529 B2 | 2/2014 | Sinha | |
| 8,794,062 B2 | 8/2014 | DiFoggio et al. | |
| 8,824,240 B2 | 9/2014 | Roberts et al. | |
| 8,850,879 B2 | 10/2014 | Swett | |
| 9,038,443 B1* | 5/2015 | Pace | G01H 13/00 73/64.53 |
| 2002/0100327 A1 | 8/2002 | Kersey et al. | |
| 2002/0178803 A1* | 12/2002 | Pelletier | E21B 47/06 73/152.47 |
| 2002/0178805 A1* | 12/2002 | DiFoggio | E21B 47/10 73/152.55 |
| 2004/0236512 A1* | 11/2004 | DiFoggio | E21B 47/10 702/6 |
| 2005/0247119 A1* | 11/2005 | DiFoggio | E21B 47/10 73/152.47 |
| 2006/0277979 A1* | 12/2006 | Fitch | G01N 11/16 73/54.41 |
| 2007/0129901 A1* | 6/2007 | DiFoggio | E21B 49/10 702/54 |
| 2007/0157737 A1 | 7/2007 | Gysling et al. | |
| 2007/0159625 A1* | 7/2007 | DiFoggio | G01J 3/02 356/328 |
| 2007/0261486 A1 | 11/2007 | Fallet | |
| 2008/0030729 A1* | 2/2008 | DiFoggio | G01J 3/02 356/328 |
| 2008/0034798 A1* | 2/2008 | Bergman | C03B 7/02 65/90 |
| 2008/0215245 A1* | 9/2008 | Reittinger | E21B 49/10 702/13 |
| 2009/0101432 A1* | 4/2009 | Hsu | G01V 1/44 181/102 |
| 2009/0110982 A1* | 4/2009 | Yoon | H01M 8/04194 429/429 |
| 2009/0165547 A1* | 7/2009 | Steinsiek | E21B 47/101 73/152.32 |
| 2009/0173158 A1* | 7/2009 | Gehring | G01N 29/022 73/590 |
| 2010/0116035 A1* | 5/2010 | Anderson | G01N 29/022 73/61.49 |
| 2011/0232374 A1* | 9/2011 | Gehring | G01N 29/022 73/64.53 |
| 2012/0055262 A1* | 3/2012 | Sinha | G01F 1/66 73/861.04 |
| 2012/0069708 A1* | 3/2012 | Swett | B06B 1/0618 367/81 |
| 2012/0239301 A1* | 9/2012 | Kischkat | G01N 9/002 702/7 |
| 2012/0285232 A1 | 11/2012 | Swett | |
| 2013/0063000 A1* | 3/2013 | Swett | G01N 29/022 310/339 |
| 2014/0182363 A1* | 7/2014 | Potyrailo | G01N 27/026 73/64.53 |
| 2015/0331132 A1* | 11/2015 | Gao | E21B 47/101 73/152.05 |
| 2016/0108729 A1* | 4/2016 | Li | G01N 11/16 702/12 |

OTHER PUBLICATIONS

International Search Report and Written Opinion dated Nov. 7, 2017, for related pct application, PCT/US2016/030586.

* cited by examiner

METHOD OF ESTIMATING MULTI-PHASE FLUID PROPERTIES IN A WELLBORE UTILIZING ACOUSTIC RESONANCE

BACKGROUND OF THE INVENTION

1. Field of Invention

The present disclosure relates to in-situ down-hole acoustic measurements in a production wellbore for determining composition and chemical properties of multi-phase fluids in the wellbore, where the multi-phase fluid measurements are based on chemometric correlations that exist between multi-phase fluid properties and the fluid acoustic properties of sound speed, bulk modulus and acoustic impedance.

2. Description of Prior Art

Fluids produced from a subterranean formation flow into a wellbore that intersects the formation, where the fluids are typically directed to the surface within production tubing. The fluids often are made up of a mixture of hydrocarbons and water, and where the hydrocarbons sometimes are a mixture of liquid and gas. Analyzing properties and/or composition of the produced fluid generally yields useful information about the formation with regard to hydrocarbon production. Further development of the formation for hydrocarbon production is usually driven by the fluid property information obtained. Further, estimates of production capacity, producing zones, production rates, and expected operational life of the wellbore are also sometimes generated based on wellbore fluid analysis. Systems for analyzing downhole production fluid properties are typically disposed at the surface, where the fluid is analyzed at a pressure and temperature that are different from when downhole. Downhole systems often include multlple sensors each of which provides a measurement for one of several fluid properties that is combined to estimate downhole oil volume fractions.

SUMMARY OF THE INVENTION

Described herein are embodiments of a method and system for estimating properties of a production wellbore fluid. One example of a method of analyzing a fluid within a wellbore includes providing a sensor that is made up of a housing, a resonant cavity in the housing, a diaphragm, and an electroactive material coupled with the diaphragm. The method further includes disposing the sensor in the wellbore, flowing fluid in the wellbore through the cavity, generating acoustic waves in the cavity by oscillating the diaphragm over a range of frequencies, measuring electrical admittance across the electroactive material for the range of frequencies, obtaining shifts in the resonant frequencies of the electrical admittance spectra due to changes in fluid properties by comparing the shifted admittance spectra with a reference admittance spectra obtained without the fluid in the cavity, and estimating a property of the fluid by substituting the values of the resonant frequency shifts in the electrical admittance spectra into an estimator equation developed chemometrically using fluids having known properties. The fluid admittance spectra can include magnitude values, real values, and imaginary values. Examples of the electroactive material are one or more of an electroactive polymer and a piezoelectric stack. The method can further include providing electricity to the electroactive material, and wherein the step of estimating shifts in resonant frequencies of admittance involves measuring a chance in electrical admittance across the electroactive material. In an example, the estimator equation was derived by simulating flowing a series fluids with known properties through the cavity, simulating oscillating the diaphragm over a range of frequencies, obtaining a known fluid admittance spectra for each of the series of fluids by obtaining simulated values of admittance through the electroactive material for each of the fluids with known properties and at selective values within the range of frequencies, estimating differences between maximum values in each of the known fluid admittance spectra with maximum values in the reference admittance spectra, conducting a statistical multi-dimensional regression analysis to identify estimator functions and algebraic relations. The fluid properties estimated can be multi-phase composite fluid sound speed, fluid density, and bulk modulus. From these multi-phase composite properties, estimates can be made for downhole fluid volume fractions, gas-oil-ratio ("GOR"), API, live-oil density, live-oil sound speed, and live-oil compressibility. The method further includes acoustic measurements that are simultaneous and congruent (i.e. measurement of the same sample of fluid at the same time) with respect to each other, thus providing a true measure of the bulk composite fluid sound speed and acoustic impedance that have correlations with compositional and chemical properties of the fluid.

An alternate method of analyzing a fluid within a wellbore includes flowing a portion of the fluid into a resonant cavity, creating standing waves in fluid in the cavity with a diaphragm that is oscillated by a piezoelectric stack, oscillating the diaphragm over a range of frequencies, measuring electrical admittance across the piezoelectric stack for the range of frequencies, obtaining shifts in the resonant frequencies of the electrical admittance spectra due to changes in fluid properties by comparing the shifted admittance spectra with a reference admittance spectra obtained by oscillating the diaphragm with the piezoelectric stack with the cavity being empty, obtaining differences of maximum values of magnitude, real values, and imaginary values between the fluid admittance spectra and the reference admittance spectra, and estimating properties of the fluid by substituting the differences into an estimator equation developed chemometrically using fluids having known properties. The method can also include providing electricity to the piezoelectric stack, and wherein the step of estimating shifts in resonant frequencies of admittance involves measuring a change in electrical admittance across the piezoelectric stack. The cavity is optionally provided in a downhole tool, the method further involving disposing the downhole tool within the wellbore. In one example, the diaphragm includes a disk portion mounted on a stem, and wherein the disk portion projects into the cavity during the step of oscillating. In an example, the fluid flowing to the cavity is directed through an inlet channel, and wherein fluid exits the cavity through an exit channel having substantially the same dimensions as the inlet channel.

Also disclosed herein is a fluid measurement system for analyzing fluid within a wellbore and which includes a sensor assembly that has a main body, a resonant cavity in the main body in communication with fluid ambient to the sensor assembly, a piezoelectric stack in the main body that is selectively oscillated over a range of frequencies when energized, and a diaphragm coupled to an end of the piezoelectric stack and disposed in the cavity, so that the diaphragm oscillates in the cavity when the piezoelectric stack is actuated. Also included with the fluid measurement system is a processor in communication with the sensor assembly that, selectively receives data representing an electrical admittance spectra that is defined by monitoring a voltage and current across the piezoelectric stack over the range of frequencies when a fluid being monitored is in the cavity, selectively receives data representing a reference admittance spectra that is defined by monitoring an electrical admittance across the piezoelectric stack over the range of frequencies when the cavity is empty, selectively obtains differences of maximum values of magnitude, real values, and imaginary values between the fluid-shifted electrical admittance spectra and the reference admittance spectra, and selectively estimates properties of the fluid by substituting the differences into an estimator equation developed chemometrically using fluids having known properties. In an example, the chamber has a generally cylindrical cross section and with a diameter that transitions radially inward away from the diaphragm. Optionally, the diaphragm includes a disk like member with upper and lower surfaces that project axially away from the piezoelectric stack with distance radially outward from a center of the diaphragm. In one alternative, the piezoelectric stack projects generally transverse to an axis of the main body and the cavity is radially offset from the axis. Channels are optionally formed through the body at ends of the cavity, wherein the channels have substantially the same dimensions. In an embodiment, the channels are formed along a path that intersects the diaphragm.

BRIEF DESCRIPTION OF DRAWINGS

Some of the features and benefits of the present invention having been stated, others will become apparent as the description proceeds when taken in conjunction with the accompanying drawings, in which.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Some algorithms have been developed to perform chemometric analyses on multi-phase fluids based on bulk fluid sound speed measurements to estimate properties such as volume fraction of the continuous and dispersed phases in the fluid medium. These methods though rely on a prior knowledge of the mass density of the continuous and dispersed phases of the flow, and have been developed primarily for surface separation systems, common within the oil and gas extraction industry. None of these approaches are applicable to in-situ downhole applications as the mass densities of the components of the flow are not generally known and are only estimable from surface "dead oil" properties that do not account for effects such as downhole pressure, temperature, and gas-saturation. Examples of a method and system described herein for estimating fluid properties acoustically examines fluids in a specific and congruent manner. That is, estimating a fluid property based on a single measurement giving the density, sound speed, and bulk modulus of the composite fluid being analyzed.

Figure 1:
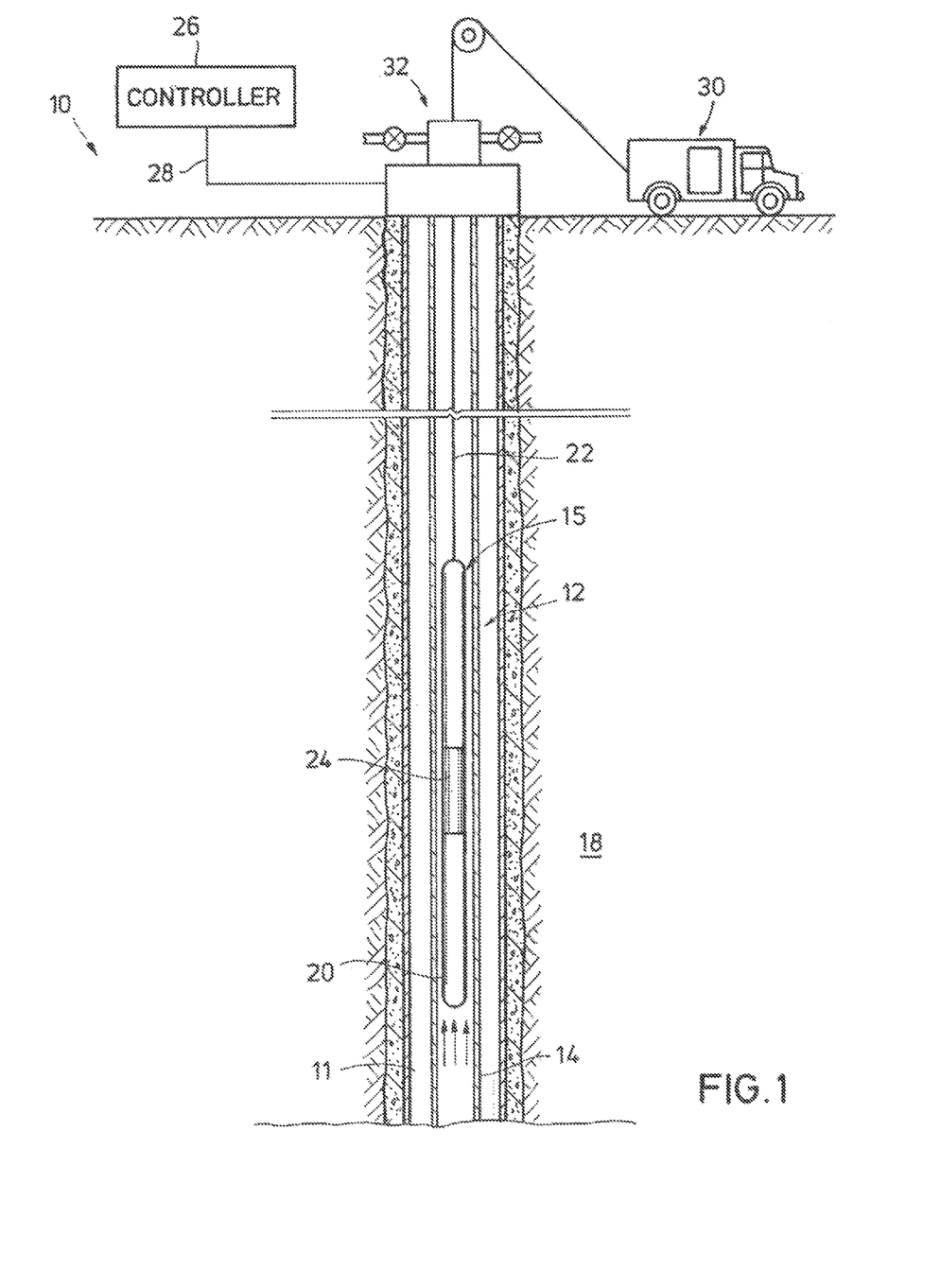
FIG. 1 is a sectional view of an example of a fluid measurement system deployed in a wellbore for measuring properties of fluid in the wellbore.

Shown in a partial side sectional view in FIG. 1 is one example of a fluid measurement system 10 that is used for monitoring fluids disposed in a wellbore 11. In this example, the fluid measurement system 10 includes a fluid measurement tool 12 shown inserted within a tubular 14. Inserting the measurement tool 12 within tubular 14 creates an annulus 15 between the measurement tool 12 and tubular 14. In the example of FIG. 1, tubular 14 is disposed within a wellbore 11, where the wellbore 11 is formed within a formation 18. Measurement tool 12 includes an outer housing 20 providing a cover and protection from downhole conditions for components of the fluid measurement tool 12, and also provides mounting surfaces for the components. A wireline 22 is illustrated for deploying measurement tool 12 within tubular 14. However, other means of deployment may readily be substituted, such as tubing, drill pipe, slick line, cable, and the like. Contained within housing 20 is a sensor assembly 24, that as explained below, provides a means of evaluating properties of fluid flowing through tubular 14 while downhole. Still referring to FIG. 1, a controller 26 is schematically illustrated on surface in optional communication with sensor assembly 24 via communication means 28. Examples of communication means 28 include signal lines, telemetry, electromagnetic waves, fiber optics, and the like. Optionally, a surface truck 30 is depicted on surface outside the opening of wellbore 11 and may be used for raising and lowering fluid measurement tool 12 within wellbore 11. A wellhead assembly 32 mounts on an upper end of wellbore 11, wherein wireline 22 threads through wellhead assembly 32.

Figure 2:
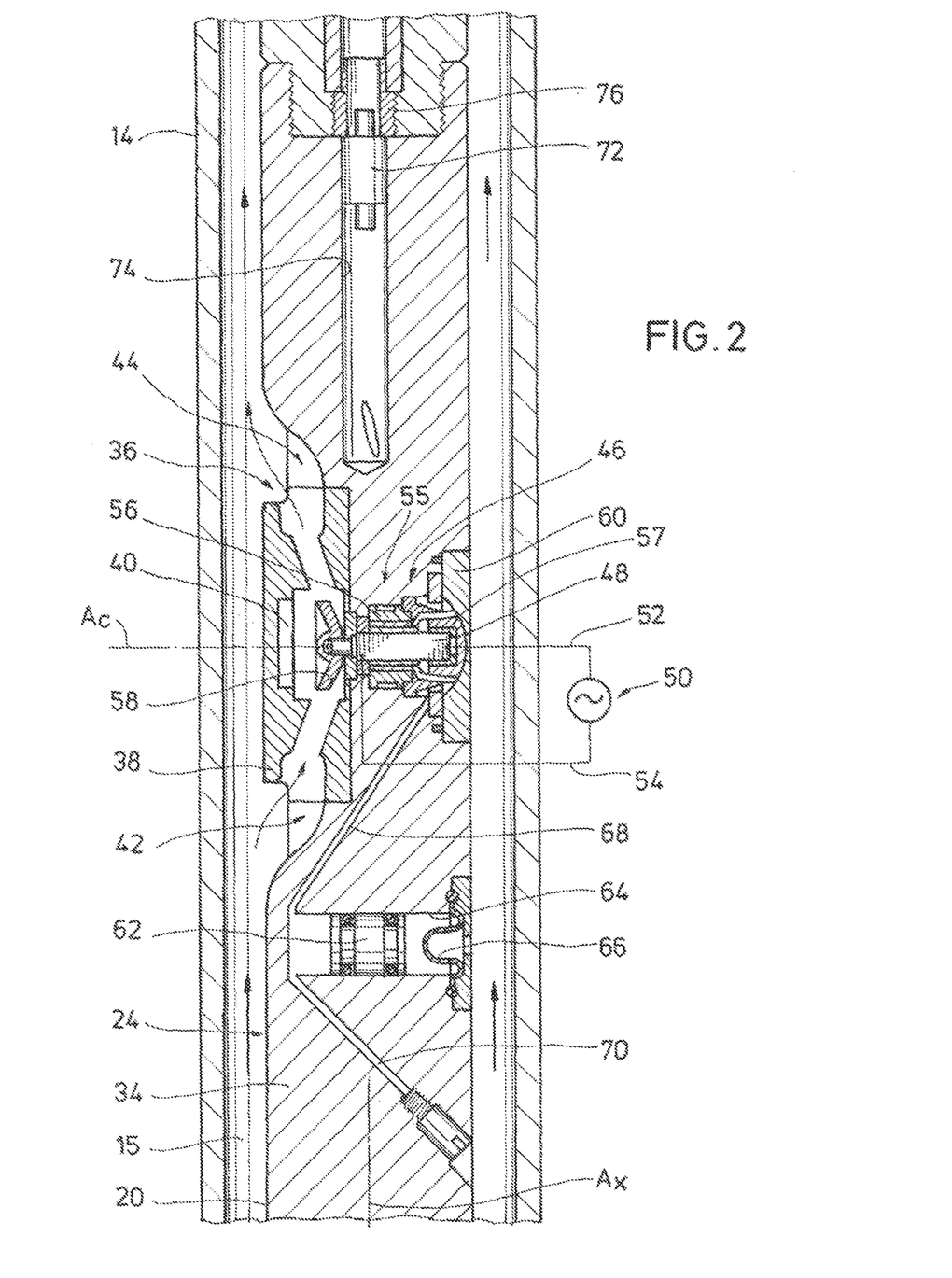
FIG. 2 is s sectional view of an example of a sensor assembly disposed in the fluid measurement system of FIG. 1.

FIG. 2 shows in a side sectional view one embodiment of sensor assembly 24 mounted within housing 20. Here, sensor assembly 24 includes a main body 34, which is a generally elongate member with a curved outer circumference. An example of a recess 36 is shown formed on a lateral side of body 34 roughly at its mid-portion, and which extends axially along a portion of its length and a portion of its circumference. An embodiment of a manifold 38 is illustrated mounted within recess 36, wherein manifold 38 has a generally curved outer surface with a radius substantially similar to a radius of the outer circumference of main body 34. Opposing axial ends of manifold 38 are generally planar and complimentary to planar surfaces formed in recess 36; where the planar surfaces lie in planes that are generally perpendicular to an axis $A_X$ of sensor assembly 24. A cavity 40 is shown formed within manifold 38 that has a generally curved outer circumference and formed along an axis $A_C$ that is generally perpendicular to axis $A_X$. A diameter of cavity 40 decreases at a transition proximate an outer surface of manifold 38, but remains substantially constant on opposing sides of the transition in the example of FIG. 2. Channels 42, 44 project axially through the opposing axial ends of manifold 38 and intersect cavity 40. As will be described in more detail below, and as illustrated by arrows within annulus 15, a flow path may be created for fluid flowing through annulus 15 through channels 42, 44 and cavity 40.

Figure 3:
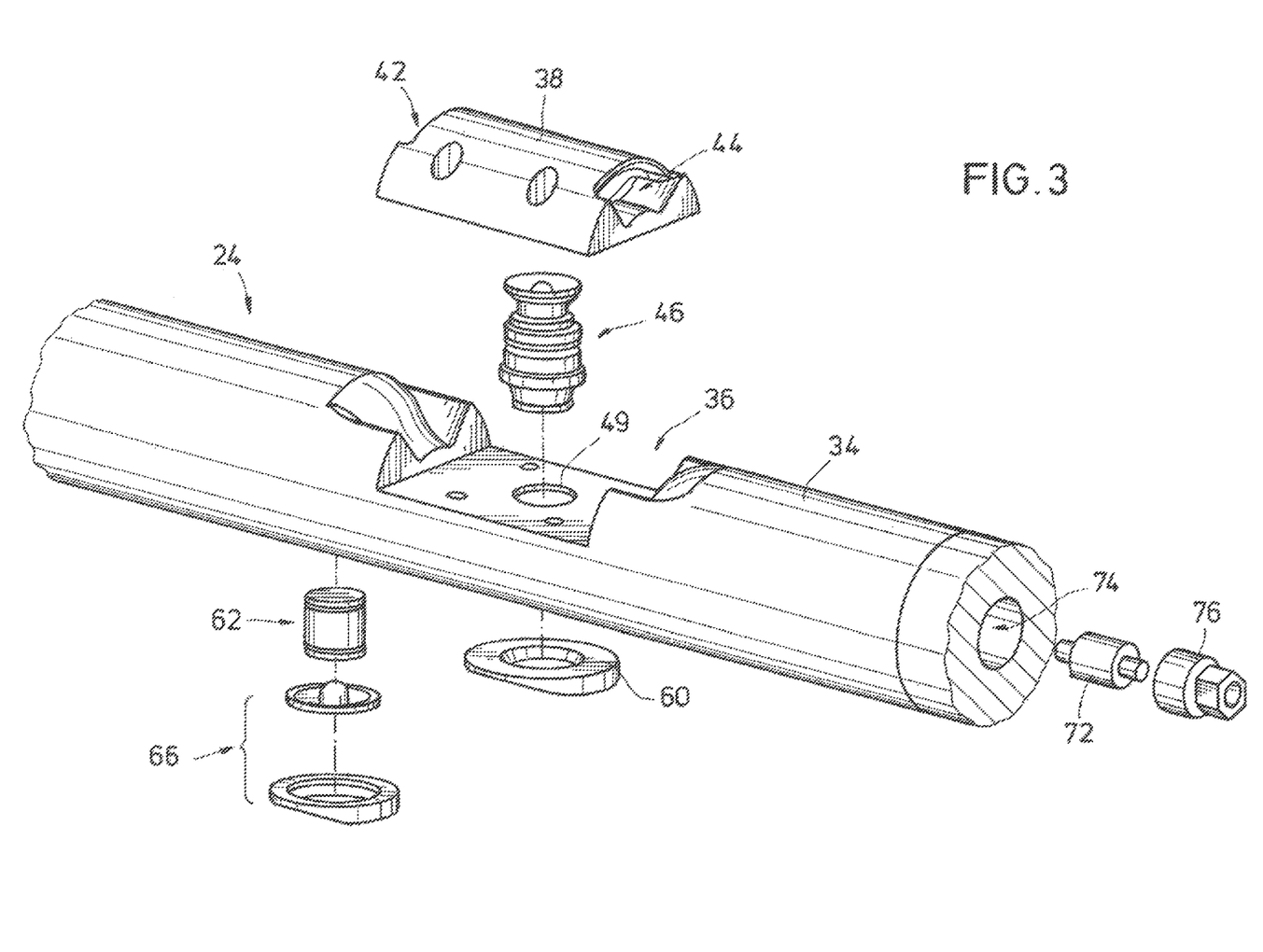
FIG. 3 is an exploded view of the sensor assembly of FIG. 2.

An example of an acoustic transducer 46 is shown transversely mounted within main body 34 and having one end that projects into cavity 40. Acoustic transducer 46 includes a piezo-electric stack 48, which is an elongate member transversely projecting from a lateral side of main body 34 and to proximate cavity 40. Piezo-electric stack 48 can be a single monolithic element made up of piezo-electric material (i.e. whose volume changes in response to an application of electrical potential), or a series of elements of piezo-electric material stacked together to form the stack 48. Embodiments exist wherein any type of electrically responsive material is substituted for the piezo-electric stack 48, such as an electroactive polymer. An opening 49 is shown (FIG. 3) on a lower surface of recess 36 and which accommodates a lower portion of acoustic transducer 46. Referring back to FIG. 2, an example of a power source 50 is schematically provided, where power source 50 is used for energizing acoustic transducer 46 (e.g. to provide voltage and/or current to the piezo-electric stack 48). Power source 50 is illustrated in selective electrical communication with opposing ends of the piezo-electric stack 48 via conductive leads 52, 54. Selectively conducting electricity between power source 50 and piezo-electric stack 48 oscillates piezo-electric stack 48. Further illustrated in FIG. 2 is a generally cylindrical housing 55 circumscribing a portion of the acoustic transducer 46. Housing 55 is made up of an upper housing 56 which coaxially mates with a lower housing 57 to provide a covering around piezo-electric stack 48. A disk like diaphragm 58 is shown coupled to an end of piezo-electric stack 48 and is disposed within cavity 40. Optionally, a cap 60 may be affixed by bolting with sealing onto an outer surface of the main body 34, on a side opposite from the recess 36, to allow for insertion and/or retrieval of the acoustic transducer 46.

Still referring to FIG. 2, a pressure equalization system is included within main body 34 so that when disposed at depths within a wellbore 11, pressure differentials can be minimized across the main body 34. In this example, a piston 62 is shown axially moveable within a cylinder 64 that is transversely formed in main body 34 and axially offset from the opening 49. A flexible membrane 66 mounts over an opening in the side of the main body 34 where cylinder 64 intersects with an outer surface of main body 34. Thus pressure ambient to the sensor assembly 24 can be communicated through the flexible membrane 66 and to cylinder 64. Pressure equalization fluid is provided within cylinder 64 so that pressure communication across membrane 66 can be transferred to piston 62 and to urge piston 62 within cylinder 64. In situations where ambient pressure exceeds pressure internal to the sensor assembly 24, piston 62 is urged away from membrane 66 and increases pressure in cylinder 64 on a side of piston 64 distal from membrane 66. A passage 68 is shown obliquely formed within main body 34 that provides pressure communication between cylinder 64 and a space adjacent acoustic transducer 46. Thus pressure ambient to the sensor assembly 24 can be transferred across piston 62, through pressure equalization fluid in cylinder 64 and passage 68, to the space adjacent acoustic transducer 62. The pressure equalization fluid within cylinder 64 and passage may be a non-conducting dielectric fluid. Another obliquely formed passage 70 can provide an optional fill line for adding fluid within cylinder 64 and passage 68. At an end of main body 34 distal from piston 62 is an electrical connector 72 that is coaxially inserted within a bore 74 that extends through an end of main body 34 and along a portion of its length. A threaded nut 76 retains connector 72 within bore 74.

Figure 4:
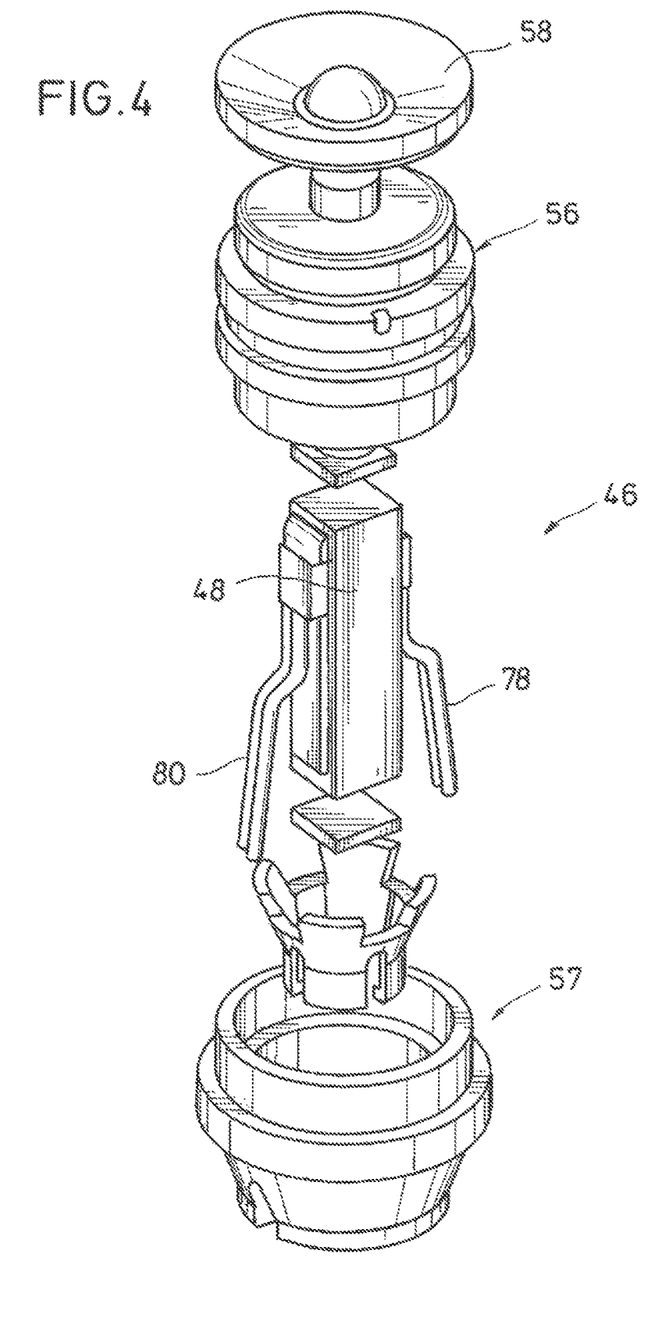
FIG. 4 is an exploded view of an example of an acoustic transducer of the sensor assembly of FIG. 2.

Referring now to FIG. 4, shown in an exploded view is one example of the acoustic transducer 46. Here, the upper and lower housing 56, 57 are spaced axially apart to reveal the piezo-electric stack 48 within. In this example, stack 48 has a generally rectangular outer surface and is elongate. Connectors 78, 80 are attached to opposing outer lateral surfaces of piezo-electric stack 48 and for providing connectivity between piezo-electric stack 48 with power source 50 (FIG. 2).

Figure 5:
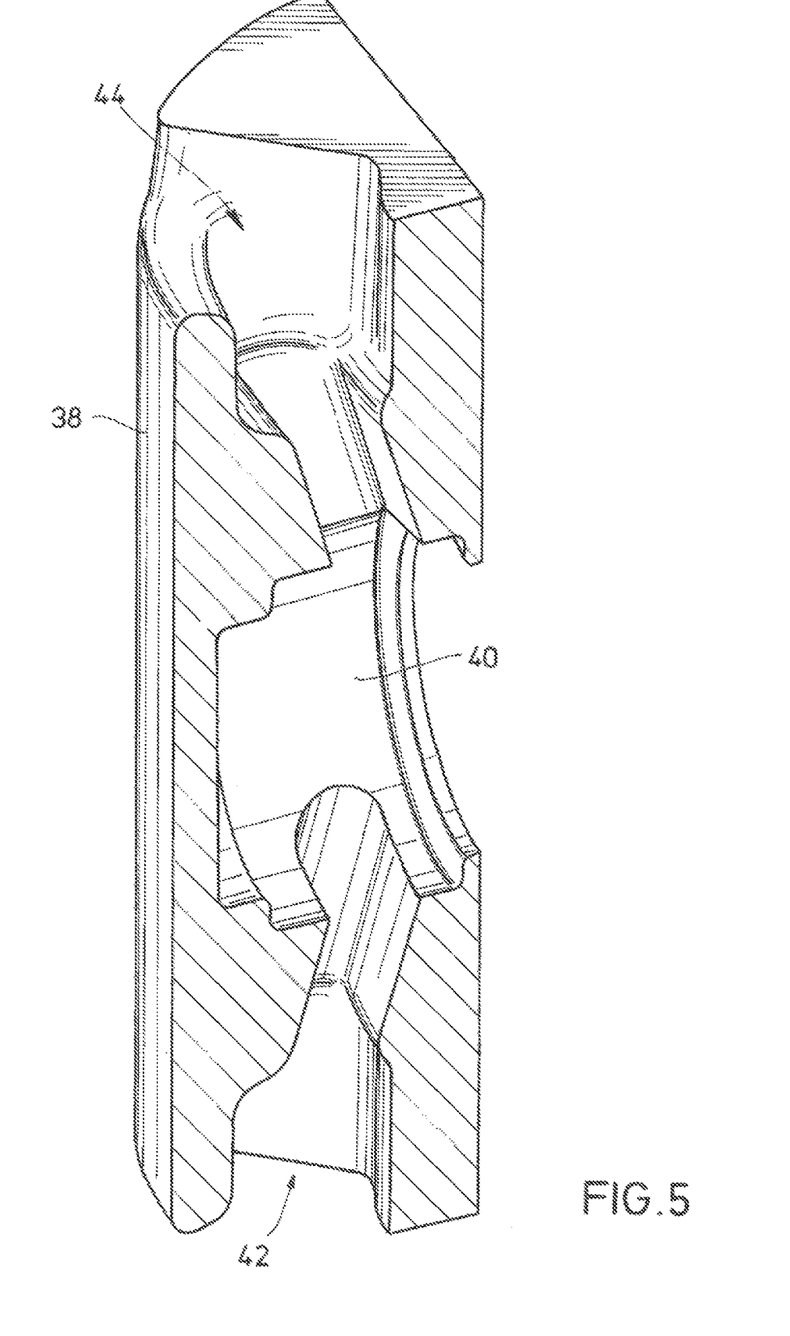
FIG. 5 is a perspective partial sectional view of an example of a manifold from the sensor assembly of FIG. 1.

FIG. 5 shows in a perspective partial cut away view one example of manifold 38 and better illustrates the intersection between channels 42, 48 and opposing ends of cavity 40. It should be pointed out, that embodiments exist wherein the dimensions of channel 42 and channel 44 are substantially the same. Moreover, fluid flow can occur in either direction through the channels 42, 44 and cavity 40. That is, in some instances channel 42 operates as an inlet to cavity and channel 44 operates as an exit from cavity 40, and other examples exist where channel 44 operates as an inlet to cavity 40, and channel 42 operates as an exit from cavity 40.

Figure 6:
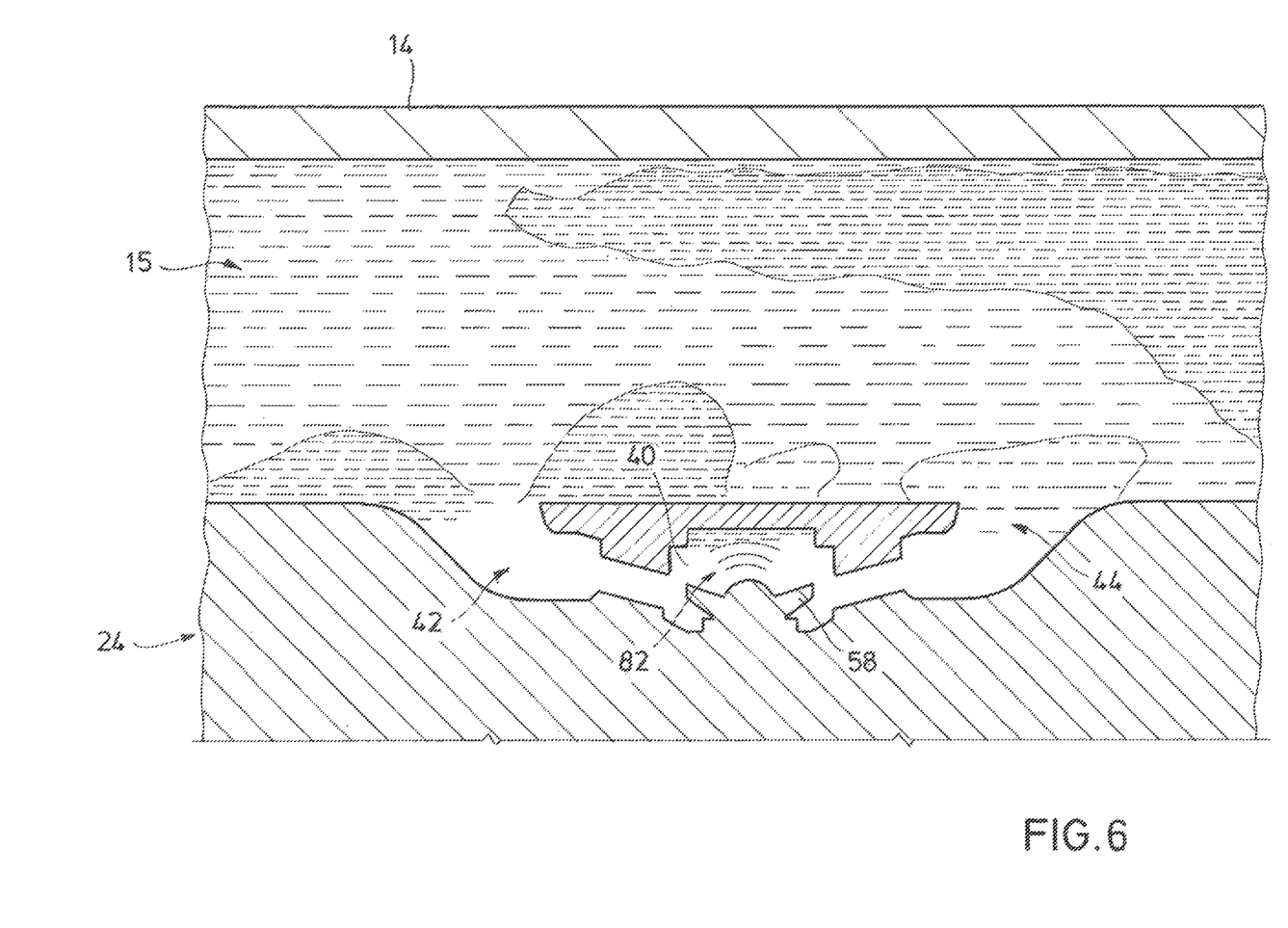
FIG. 6 is a side sectional view of a schematic example of operation of the sensor assembly of FIG. 2.

FIG. 6 is a side sectional view that schematically illustrates an example of fluid flowing through annulus 15 and while diaphragm 58 is being oscillated within cavity 40. In this example, the diaphragm 50 is being oscillated at different frequencies for a set period of time. Further, at each of these frequencies, standing waves 82, which are schematically illustrated within cavity 40, may be formed within the fluid in cavity 49. Different shadings within annulus 15 represent simulated velocities of fluid flowing axially through annulus, a portion of the fluid is diverted into channel 42, flows into cavity 40, to channel 44, and then back into annulus 15.

Figure 7:
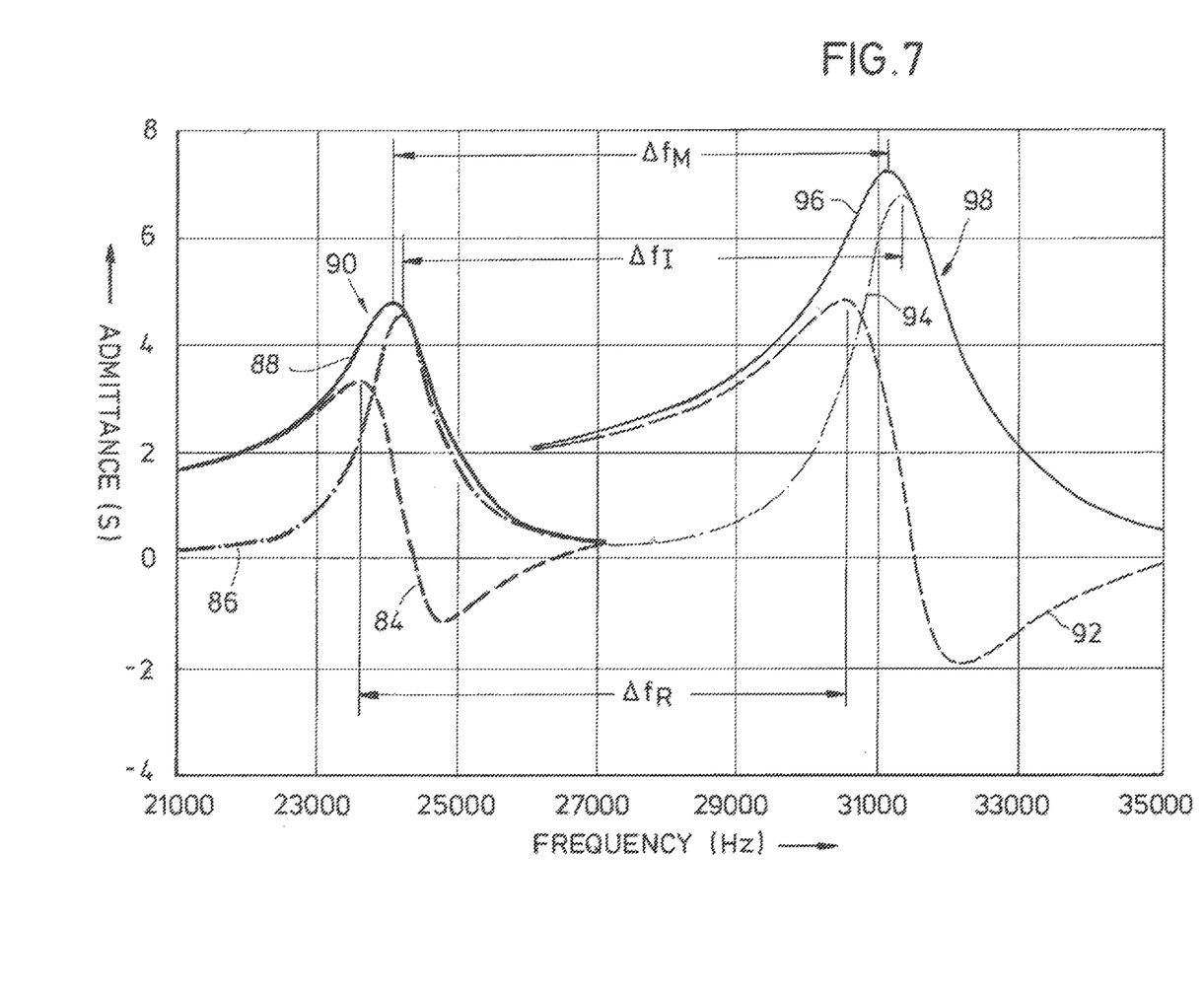
FIG. 7 is a chart having plots of examples of admittance spectra of a piezo-electric stack for use with the sensor assembly of FIG. 2.

In an example of operation, as the diaphragm 58 is being oscillated along a range of frequencies, the electrical admittance across piezo-electric stack 48 (FIG. 2) is monitored and a corresponding complex admittance value at each frequency is obtained. In the embodiment of FIG. 7, a curve 84 represents real values of admittance that were obtained over that range of frequencies. Similarly, curve 86 represents imaginary values of admittance taken over that same range of frequencies, and curve 88 represents the magnitude of those values of admittance. Curves 84, 86, 88 define a fluid admittance spectra 90. A similar series of curves 92, 94, 96 shown in FIG. 7 represent admittance values measured across the piezo-electric stack 48 by oscillating diaphragm 58 within cavity 40, when cavity 40 is empty and void of fluid. Optionally, the cavity 40 in this example may be gas filled, or may be evacuated and void of any substance. Curve 92, which represents the real value of admittance when the cavity 40 is empty, curve 94 shows the corresponding imaginary values of admittance, and curve 96 represents the magnitude of admittance values taken over the range of frequencies illustrated in FIG. 7. A combination of curves 92, 94, 96 define a reference admittance spectra 98. Further shown in FIG. 7 are differences in frequencies, represented as $\Delta f_M$, $\Delta f_I$, $\Delta f_R$, and which are the respective differences between the maximum values of the curves 84, 86, 88, and curves 92, 94, 96.

In one non-limiting example, a statistical analysis model was created by obtaining simulated values of the fluid admittance spectra, as described above, for a number of different fluids having known densities and known sound speeds. In this example, a data set of frequency shift triplets (i.e. differences in real, imaginary, and magnitude peak frequencies) was developed for a set of 32 unique fluid acoustic property combinations. More specifically, the data set simulated "calibration fluids", where each calibration fluid had a different sound speed, and different fluid density. In this example, the values of sound speed ranged from about 500 m/s to about 1500 m/s, and the values of the fluid density ranged from about 500 kg/m$^3$ to about 1250 kg/m$^3$. The analytical data was incorporated in a series of multi-regression statistical analyses to determine intrinsic characteristic functions and corresponding algebraic relations that would predict cavity fluid bulk acoustic properties that correspond to the shifts in electrical admittance spectra resonant frequency of the sensor assembly 24 illustrated in FIGS. 2 and 6. In developing the algebraic relations that form the fluid properties prediction algorithm, a set of functions was developed that included the shifts in resonant frequencies, the differences in shifts in resonant frequencies, and various products of shifts and differences in shifts of resonant frequencies. These sets of functions were incorporated in the multi-regression statistical analysis using the statistical analyses software package Statistica®, published by the StatSoft Corporation. It was found that high correlations exist between these types of functions of a resonant cavity acoustic impedance sensor response spectra and a set of cavity fluid bulk acoustic properties. Example of this multi-regression statistical analysis is provided in DiFoggio, U.S. Pat. No. 8,032,311, which is assigned to the assignee of the present application, and which is incorporated herein in its entirety for all purposes. While a computer simulation was used to generate the simulated values by modeling fluid flow through the sensor assembly, these values are also attainable by monitoring resonant frequencies of electrical admittance through an actual sensor assembly 24 with fluid flow.

A set of live-oil properties estimator equations was developed from chemometric analyses of a virtual borehole fluid properties data set developed from the widely adapted Batzle-Wang empirical relations (Batzle & Wang, 1992) for gas-saturated oil and brine fluids, and the Urick density model (Urick, 1947) coupled with the Woods equation for compressibility to calculate multi-phase bulk fluid properties. The predictive accuracy of the estimator equations was evaluated from an independent virtual borehole fluid data set of 11,130 fluid samples developed using the Batzle-Wang, Urick, and Woods relations employed in development of the original virtual data set. The developments are described and the estimators defined in the form of algebraic functions.

Applying the statistical analysis technique described above, estimator equations were developed that correlate functions of measured admittance spectra (FIG. 7) resonant frequency shifts for each of the following fluid characteristics: composite fluid sound speed, composite fluid density, and composite fluid bulk modulus. These estimator equations for composite fluid properties were then applied in similar multi-regression analyses to develop estimator equations for constituent fluid properties such as live oil sound speed, live oil bulk modulus, live oil mass density, live oil API density, gas oil ratio ("GOR"), and oil water holdups. Accordingly, in one example of use, the sensor assembly 24 is operated as described above (FIG. 6) by oscillating the diaphragm 58 over a range of frequencies while a fluid is diverted into the cavity 40; where properties of the fluid are not known. Frequency shift triplets are generated in the same manner as discussed above, but that correlate to the properties of the actual unknown fluid being monitored with the sensor assembly 24. The values of the shift triplets are substituted into the estimator equations to obtain the particular composite fluid properties of the unknown flow. An advantage of the sensor assembly 24 is that it can analyze fluid in a simultaneous and congruent manner, that is more than one fluid property can be estimated from the same measurement. Thus deploying the sensor assembly 24 within the wellbore 11 (FIG. 1) and flowing wellbore fluid in the annulus 15, the fluid can be analyzed in real time, in-situ, and without any prior knowledge thereof, so that the fluid properties of the composite flow listed above can be estimated.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, the piezo-electric stack 48 (or other electrically responsive material) and diaphragm 58 could be contained wholly within the opening 49. Optionally, the diaphragm 58 can be a membrane that sets on the lower surface of the recess 36 and only enters the cavity 40 during an expansion stroke of the piezo-electric stack 48. Moreover, alternative configurations of the cavity 40 include a dome like shape, or one where its diameter is constant along its entire height. These and other similar modifications that develop appropriate resonant cavity characteristics will readily suggest themselves to those skilled in the art, and are intended to be encompassed within the spirit of the present invention disclosed herein and the scope of the appended claims.

What is claimed is:

1. A method of analyzing a fluid within a wellbore comprising:
   providing a sensor that comprises, a housing, a resonant cavity in the housing, an inlet to the cavity, an outlet from the cavity, a diaphragm, and an electroactive material coupled with the diaphragm;
   disposing the housing in a path of fluid flowing in the wellbore so that a portion of the fluid flowing in the wellbore flows from an annulus between the housing and walls of the wellbore, enters the cavity through the inlet, flows through the cavity, and flows back into the annulus through the outlet;
   generating acoustic waves in the fluid flowing through the cavity by oscillating the diaphragm over a range of frequencies;

measuring electrical voltage and current across the electroactive material for the range of frequencies to obtain an electrical admittance spectra corresponding to the fluid flow;

obtaining shifts in resonant frequencies of electrical admittance spectra by comparing the admittance spectra of the fluid flow with a reference admittance spectra obtained without the fluid in the cavity;

obtaining an estimator equation generated by, (a) comparing a number of different simulated admittance spectra with the reference admittance spectra, where each of the different simulated admittance spectra represents simulated values of admittance obtained for a particular fluid disposed in the cavity having a known density and sound speed, and where the admittance spectrum for each particular fluid is decomposed into the real, imaginary, magnitude, and phase components over a resonance frequency bandwidth, (b) developing a set of functions that include shifts in resonance frequencies of admittance components between each of the number of different simulated admittance spectra and reference admittance spectra, the differences in shifts in resonance frequencies of admittance components between each of the number of different simulated admittance spectra and reference admittance spectra, and products of shifts and differences in resonance frequencies of admittance components between each of the number of different simulated admittance spectra and reference admittance spectra, and (c) utilizing the set of functions in a series of multi-regression statistical analyses to determine the estimator equation; and estimating a property of the fluid by substituting the value of the resonant frequencies' shifts in electrical admittance spectra into the estimator equation.

2. The method of claim 1, wherein the electrical admittance spectra associated with the resonant cavity comprises magnitude values, real values, and imaginary values.

3. The method of claim 1, wherein the electroactive material comprises one or more of an electroactive polymer or a piezoelectric stack.

4. The method of claim 1, further comprising providing electricity to the electroactive material, and wherein the step of measuring electrical admittance comprises measuring a change in voltage and current across the electroactive material.

5. The method of claim 1, wherein the estimator equation was derived by simulating flowing a series of fluids with known properties through the cavity, simulating oscillating the diaphragm over a range of frequencies, obtaining a known electrical admittance spectra for each of the series of fluids by obtaining simulated values of electrical admittance through the electroactive material for each of the fluids with known properties and at selective values within the range of frequencies, estimating differences between maximum values in each of the electrical admittance spectra for each known fluid with maximum values in the reference electrical admittance spectra, conducting a multi-regression statistical analysis to identify estimator functions and algebraic relations.

6. The method of claim 1, wherein the fluid properties comprise parameters selected from the group consisting of composite fluid sound speed, composite fluid density, composite fluid bulk modulus, live oil sound speed, live oil bulk modulus, live oil mass density, live oil American Petroleum Institute density, gas oil ratio, and oil-water holdup.

7. The method of claim 1, wherein the fluid property comprises sound speed, the method further comprising estimating fluid density, and wherein the fluid sound speed and fluid density were obtained from a measurement of the same sample of fluid at the same time and within the cavity.

8. A method of analyzing a fluid within a wellbore comprising:

a) diverting a portion of fluid flowing inside the wellbore into a cavity;

b) creating standing waves in the fluid diverted into the cavity with a diaphragm that is oscillated by a piezoelectric stack;

c) oscillating the piezoelectric stack over a range of frequencies by conducting electricity to the piezoelectric stack from a power source;

d) monitoring an admittance across the piezoelectric stack over the range of frequencies to define a fluid admittance spectra;

e) comparing the fluid admittance spectra with a reference admittance spectra that was generated by oscillating the piezoelectric stack over a range of frequencies with the cavity being empty, the admittance spectrum for each particular fluid is decomposed into the real, imaginary, magnitude, and phase components over a resonance frequency bandwidth;

f) obtaining an estimator equation generated by, (i) comparing the reference admittance spectra with a number of simulated admittance spectra for different known fluids disposed in the cavity, the simulated admittance spectra for different known fluids represents simulated values of admittance obtained for a particular fluid disposed in the cavity having a known density and sound speed, (ii) developing functions that are dependent on a variation of resonance frequencies of admittance components between each of the number of different simulated admittance spectra and reference admittance spectra, and (iii) utilizing the functions in a series of multi-regression statistical analyses to determine the estimator equation;

g) obtaining differences of maximum values of magnitude, real values, and imaginary values between the fluid admittance spectra and the reference admittance spectra; and h) estimating properties of the fluid by substituting the differences obtained in step (g) into the estimator equation of step (f).

9. The method of claim 8, wherein the cavity s provided in a downhole tool, the method further comprising disposing the downhole tool within the wellbore.

10. The method of claim 8, wherein the diaphragm comprises a disk portion mounted on a stem, and wherein the disk portion projects into the cavity during the step of oscillating.

11. The method of claim 8, wherein the variations of resonance frequencies of admittance components between each of the number of different simulated admittance spectra and reference admittance spectra comprise, shifts in resonance frequencies of admittance components between each of the number of different simulated admittance spectra and reference admittance spectra, the differences in shifts in resonance frequencies of admittance components between each of the number of different simulated admittance spectra and reference admittance spectra, and products of shifts and differences in resonance frequencies of admittance components between each of the number of different simulated admittance spectra and reference admittance spectra.

12. A fluid measurement system for analyzing fluid within a wellbore comprising:
 a sensor assembly comprising,
  a main body,
  a cavity in the main body in communication with fluid ambient to the sensor assembly,
  an inlet and outlet in the cavity so that a portion of fluid flowing in the wellbore into the cavity via the inlet, and back into the wellbore through the outlet;
  a solid piezoelectric stack in the main body that is selectively oscillated over a range of frequencies when energized, and
  a diaphragm coupled to an end of the piezoelectric stack and disposed in the cavity, so that the diaphragm oscillates in the cavity when the piezoelectric stack is oscillated; and
 a processor in communication with the sensor assembly that,
  selectively receives data representing an electrical admittance spectra associated with the fluid that is defined by monitoring an electrical admittance across the piezoelectric stack over the range of frequencies when a fluid being monitored is in the cavity,
  selectively receives data representing a reference electrical admittance spectra that is defined by monitoring an electrical admittance across the piezoelectric stack over the range of frequencies when the cavity is empty,
  selectively obtains differences of maximum values of magnitude, real values, and imaginary values between the electrical admittance spectra of the fluid and the reference electrical admittance spectra, and
  selectively estimates properties of the fluid by substituting values of the resonant frequency shifts into an estimator equation that was generated by, (a) comparing a number of different simulated admittance spectra with the reference admittance spectra, where each of the different simulated admittance spectra represents simulated values of admittance obtained for a particular fluid disposed in the cavity having a known density and sound speed, and where the admittance spectrum for each particular fluid is decomposed into the real, imaginary, magnitude, and phase components over a resonance frequency bandwidth, (b) developing a set of functions that include shifts in resonance frequencies of admittance components between each of the number of different simulated admittance spectra and reference admittance spectra, the differences in shifts in resonance frequencies of admittance components between each of the number of different simulated admittance spectra and reference admittance spectra, and products of shifts and differences in resonance frequencies of admittance components between each of the number of different simulated admittance spectra and reference admittance spectra, and (c) utilizing the set of functions in a series of multi-regression statistical, analyses to determine the estimator equation.

13. The fluid measurement system of claim 12, wherein the cavity has a generally cylindrical cross section and with a diameter that transitions radially inward away from the diaphragm, and wherein the cavity is in fluid communication with the fluid via passages that extend from opposing ends of the cavity and are substantially symmetric about an axis that intersects the diaphragm.

14. The fluid measurement system of claim 13, wherein the passages extend away from the cavity along paths that are oblique to the axis.

15. The fluid measurement system of claim 12, wherein the piezoelectric stack projects generally transverse to an axis of the main body and the cavity is radially offset from the axis.

16. The fluid measurement system of claim 12 further comprising channels formed through the body at ends of the cavity, wherein the channels have substantially the same dimensions.

17. The fluid measurement system of claim 16, wherein the channels are formed along a path that intersects the diaphragm.

* * * * *